United States Patent
Li et al.

(10) Patent No.: US 10,768,083 B2
(45) Date of Patent: Sep. 8, 2020

(54) TEST DEVICE AND TEST METHOD OF FRACTURED ROCK MASS COLLAPSE AND ROCKFALL AND FRACTURE WATER INRUSH

(71) Applicant: SHANDONG UNIVERSITY, Jinan, Shandong (CN)

(72) Inventors: Shucai Li, Jinan (CN); Liping Li, Jinan (CN); Shaoshuai Shi, Jinan (CN); Zongqing Zhou, Jinan (CN); Hongliang Liu, Jinan (CN); Jie Hu, Jinan (CN); Shangqu Sun, Jinan (CN); Jing Wang, Jinan (CN); Wenfeng Tu, Jinan (CN); Zhijie Wen, Jinan (CN)

(73) Assignee: SHANDONG UNIVERSITY, Jinan (CN)

( * ) Notice: Subject to any disclaimer, the term of this patent is extended or adjusted under 35 U.S.C. 154(b) by 0 days.

(21) Appl. No.: 16/314,607

(22) PCT Filed: Sep. 13, 2017

(86) PCT No.: PCT/CN2017/101652
§ 371 (c)(1),
(2) Date: Dec. 31, 2018

(87) PCT Pub. No.: WO2018/050079
PCT Pub. Date: Mar. 22, 2018

(65) Prior Publication Data
US 2019/0285525 A1    Sep. 19, 2019

(30) Foreign Application Priority Data
Sep. 14, 2016    (CN) .......................... 2016 1 0823088

(51) Int. Cl.
*G01N 3/00*    (2006.01)
*G01N 3/36*    (2006.01)
(Continued)

(52) U.S. Cl.
CPC ............... *G01N 3/36* (2013.01); *G01N 3/12* (2013.01); *G01N 33/24* (2013.01); *E02D 19/06* (2013.01);
(Continued)

(58) Field of Classification Search
CPC .......... G01N 3/36; G01N 3/12; G01N 33/24; G01N 2203/0019; G01N 2203/0048; G01N 2203/0067; E02D 19/06
(Continued)

(56) References Cited

U.S. PATENT DOCUMENTS 3,958,767 A * 5/1976 Stiles ........................ B02C 1/00
241/101.76
5,145,118 A * 9/1992 Canada ............... B02C 19/0031
241/275
(Continued)

FOREIGN PATENT DOCUMENTS

CN    102607941 A    7/2012
CN    103091222 A    5/2013
(Continued)

OTHER PUBLICATIONS

Oct. 26, 2017 Office Action issued in Chinese Patent Application No. 201610823088.6.
(Continued)

*Primary Examiner* — Max H Noori
(74) *Attorney, Agent, or Firm* — Oliff PLC

(57) ABSTRACT

A test device and a test method of fractured rock mass collapse and blockfall and fracture water inrush includes a fractured rock mass preparation device, a water source loading device, a surrounding rock pressurization device and a slide rail, wherein the fractured rock mass preparation device is fixed at one end of the slide rail, and the water source loading device is fixed on the other side of the slide
(Continued)

rail. An opening is formed in the rock mass water storage structure, and the size of the opening is adapted to the size of the fractured rock mass; the surrounding rock pressurization device includes one bracket and a pressurization structure arranged below the bracket, and a space for accommodating the fractured rock mass is reserved below the pressurization structure; and the bottom support and the bracket are both movably installed on the slide rail.

13 Claims, 4 Drawing Sheets

(51) Int. Cl.
*G01N 3/12* (2006.01)
*G01N 33/24* (2006.01)
*E02D 19/06* (2006.01)

(52) U.S. Cl.
CPC ........... *G01N 2203/0019* (2013.01); *G01N 2203/0048* (2013.01); *G01N 2203/0067* (2013.01)

(58) Field of Classification Search
USPC .......................................................... 73/788
See application file for complete search history.

(56) References Cited

U.S. PATENT DOCUMENTS

| | | | | |
|---|---|---|---|---|
| 5,967,431 A | * | 10/1999 | Stafford | ............... B02C 2/005 |
| | | | | 241/207 |
| 2014/0010603 A1 | * | 1/2014 | Blais | .................. B60P 1/60 |
| | | | | 406/39 |
| 2016/0320267 A1 | * | 11/2016 | Cho | ..................... E21B 10/43 |

FOREIGN PATENT DOCUMENTS

| | | |
|---|---|---|
| CN | 103994899 A | 8/2014 |
| CN | 204142710 U | 2/2015 |
| CN | 104807960 A | 7/2015 |
| CN | 105628463 A | 6/2016 |
| CN | 105738216 A | 7/2016 |
| CN | 105758730 A | 7/2016 |
| CN | 105806686 A | 7/2016 |
| CN | 106198934 A | 12/2016 |
| FR | 2 347 526 A1 | 11/1977 |
| GB | 1572556 A | 7/1980 |
| JP | H09-209349 A | 8/1997 |

OTHER PUBLICATIONS

Oct. 18, 2017 Search Report issued in Chinese Patent Application No. 201610823088.6.
Dec. 22, 2017 Written Opinion of the International Searching Authority issued in International Patent Application No. PCT/CN2017/101652.
Dec. 22, 2017 Search Report issued in International Patent Application No. PCT/CN2017/101652.

\* cited by examiner

TEST DEVICE AND TEST METHOD OF FRACTURED ROCK MASS COLLAPSE AND ROCKFALL AND FRACTURE WATER INRUSH

FIELD OF THE INVENTION

The present invention relates to a test device and a test method of fractured rock mass collapse and rockfall fracture water inrush. The structures for rock collapse and fracture water inrush can be integrated in one device, and the research on the two disasters is achieved.

BACKGROUND OF THE INVENTION

With the rapid development of economy in China, national investment in infrastructure construction increases. More and more water conservancy and hydropower projects and tunnel projects have been carried out in the southwestern China, wherein there are a large number of underground projects. Collapse and water inrush are common forms of disasters in underground projects. Collapse is a process of losing stability and falling of the rock mass of the vault, and water inrush is a phenomenon of a large amount of water burst of water storage structures or underground rivers through water guiding structures. No matter in a construction process or in an operation period, collapse and water inrush of the underground projects will cause huge losses to lives and properties of people. An underground project model test means that the actual project is scaled down to a model according to the similarity ratio and similarity theory, and a corresponding test is performed on a scaled-down model or undistorted model to obtain related data so as to arrive at related conclusions. This has become one of the main research methods in the field of underground projects. The researches on the underground project collapse and rockfall mechanism and the rock fracture water inrush mechanism have important guiding significance for disaster prevention and reduction of the underground projects. The previous model tests have few research on the underground project collapse and rockfall mechanism and the rock fracture water inrush mechanism, or the model test research is only performed on the water inrush of the underground projects in a single aspect, and a test device that can meet the dual experimental demands of collapse and rockfall mechanism research and rock fracture water guiding mechanism research does not exist.

SUMMARY OF THE INVENTION

In order to solve the technical problems existing in the prior art, the present invention provides a test device and a test method of fractured rock mass collapse and rockfall and fracture water inrush.

In order to achieve the above objective, the technical solution adopted by the present invention is as follows:

A fractured rock mass preparation device for a fractured rock mass test includes an upper die, a lower die, a bottom support and a cutterhead, wherein the lower die is fixed on the bottom support, and the upper die is located above the lower die; the upper die, the lower die and the bottom support constitute a molding cavity of a simulative rock mass; the cutterhead is movably installed on the lower die through a guide rail which is horizontally arranged; and after the rock mass is formed, the cutterhead slides toward the rock mass to cut the rock mass to obtain the fractured rock mass.

A test device of fractured rock mass collapse and rockfall and fracture water inrush includes a fractured rock mass preparation device, a water source loading device, a surrounding rock pressurization device and a slide rail, wherein the fractured rock mass preparation device is fixed at one end of the slide rail, and the water source loading device is fixed on the other side of the slide rail;

the fractured rock mass preparation device includes a template, a cutterhead and a bottom support, the template being arranged above the bottom support, and the cutterhead being installed on a side face of the bottom support for cutting the formed rock mass to form the fractured rock mass;

the water source loading device includes a water source and a rock mass water storage structure, a water pump being connected between the water source and the rock mass water storage structure, an arched opening being formed in the rock mass water storage structure, and the size of the arched opening being adapted to the size of the fractured rock mass;

the surrounding rock pressurization device includes at least one bracket and a pressurization structure arranged below the bracket, a space for accommodating the fractured rock mass being reserved below the pressurization structure; and the bottom support and the bracket are both movably installed on the slide rail.

When the formed fractured rock mass slides to the arched opening of the rock mass water storage structure to form seal fit, a test device for simulating fracture water inrush is formed, and the water pressure in the rock mass water storage structure is controlled through the water pump to simulate the fracture water inrush under different water pressures.

When the fractured rock mass is pressurized by the surrounding rock pressurization device, the demands of surrounding rock crustal stress in different environments can be simulated, and then the collapse and rockfall of the fractured rock mass can be simulated.

When the water source loading device and the surrounding rock pressurization device are used at the same time, the situations of collapse and rockfall of the fractured rock mass and the fracture water inrush can be simulated under the surrounding rock crustal stress in different environments and under different water pressures.

Preferably, the arched template includes an upper die and a lower die, the lower die is installed on a bottom bracket, and the upper die, the lower die and the bottom bracket form a molding cavity of the arched rock mass.

Further preferably, the upper die is provided with a material injection port.

Further preferably, the upper surface of the lower die is a semi-cylindrical molding surface, and the chamber of the upper die is arched.

Further preferably, the cutterhead is movably installed on the lower die by the guide rail and is movable in the horizontal direction along the lower die; and the length of the lower die is greater than that of the cutterhead.

Firstly, the arched rock mass is prepared by the arched template, and after the arched rock mass is prepared, the cutterhead is slid to cut the arched rock mass on the lower die to generate the fractured rock mass. The cutterhead is installed on the lower die, thereby being more convenient for cutting the rock mass, improving the cutting efficiency, and saving time and labor.

Further preferably, the upper die is installed on a frame, and a telescopic rod is connected between the upper die and the frame.

The telescopic rod easily controls the ascending and descending of the upper die, and is convenient for the preparation of the arched rock mass and the separation of the upper die and the arched rock mass.

Further preferably, the lower die is placed on two groups of bottom brackets, which are a first group of bottom brackets and a second group of bottom brackets. The first group of bottom brackets is fixed at an end of the slide rail, and the second group of bottom brackets is movably installed on the slide rail. The upper die, the lower side and the second group of bottom brackets constitute the molding cavity of the arched rock mass.

After the fractured rock mass is formed, the second group of bottom brackets can drive the fractured rock mass to slide to separate from the lower die, and the fractured rock mass can also slide to the position of the water source loading device and/or the surrounding rock pressurization device to perform corresponding tests.

Preferably, the cutterhead is provided with a plurality of blades, and the blades are arranged in a stagger manner to generate joint fissures.

Further preferably, the angles of the blades on the cutterhead are adjustable to generate different joint fissures.

Preferably, the rock mass water storage structure is arched, and an arched water storage tank is formed in the rock mass water storage structure.

Preferably, the bracket is a steel frame.

Further preferably, the top inner surface of the steel frame is arched.

Still further preferably, the pressurization structure includes multiple groups of pressurization devices, each group of pressurization devices includes a hydraulic jack and a curved plate, one end of the hydraulic jack being fixed on the lower surface of the steel frame, and the other end of the hydraulic jack being fixedly connected with the curved plate.

Since the top end of the tunnel is also arched, the lower surface of the steel frame is designed to be arched, and the pressurized structure such as the hydraulic jack is installed on the inner side of the arched steel frame, so that the pressure situation of the tunnel can be better simulated. The collapse is simulated, and the situations of the collapse and rockfall and fracture water inrush of the tunnel under the action of pressurization can be simulated more accurately.

Still further preferably, the multiple groups of pressurization devices are arranged in a row, and the plurality of curved plates are connected into an arch shape.

The plurality of curved plates are connected into the arch shape to achieve uniform pressurization of the fractured rock mass.

A test method of fractured rock mass collapse and rockfall and fracture water inrush includes the following steps:

1) injecting similar materials into the dies to prepare a simulative rock mass, and separating the upper die from the simulative rock mass;

2) sliding the cutterhead toward the simulative rock mass to cut the rock mass to obtain the fractured rock mass;

3) separating the fractured rock mass from the lower die;

4) moving the fractured rock mass to the rock mass water storage structure, and sealing the fractured rock mass with the opening of the rock mass water storage structure;

5) injecting water into the rock mass water storage structure, and adjusting the internal water pressure to perform a fracture water inrush test;

6) pressurizing the fractured rock mass by using the surrounding rock pressurization device to perform a fracture collapse test;

or pressurizing the fractured rock mass during the fracture water inrush test; and the order of the above steps can be adjusted as long as the test is not affected.

The present invention has the following beneficial effects:

1. A fluid-like similar material, such as hot melt paraffin, is solidified to simulate the rock mass, and the solidified material can be recycled after being melted.

2. The rock fractures are cut by the cutterhead with adjustable blade angles, and different groups of joint fissures can be generated by adjusting the blade angles of the cutterhead.

3. The steel frame, the steel rack and the rack bottom plate are spliced by high-strength steel components through reserved bolt slots, thereby being detachable and capable of meeting the strength requirements.

4. The hydraulic jack installed in the steel rack acts on the surface of the formed simulative rock mass through the curved plates, and the exerting force of the jack is adjusted through a numerical control system to simulate the demand of surrounding rock crustal stress in different environments.

5. The rock mass water storage structure is designed in the steel rack, and the shape of the rock mass water storage structure is consistent with that of the simulative fractured rock mass. The rock mass water storage structure can be closely fit to the fractured rock mass, and the influence of water pressure on the water inrush criteria can be researched by adjusting the water pressure in the rock mass water storage structure.

Reference signs: 1 material injection port; 2 upper die; 3 cutterhead; 4 bottom support; 5 telescopic rod; 6 steel frame; 7 hydraulic jack; 8 curved plate; 9 bottom plate; 10 slide rail; 11 pressurization water pump; 12 water storage tank; 13 water guide tube; 14 steel rack; 15 rock mass water storage structure; 16 fractured rock mass.

DETAILED DESCRIPTION OF THE EMBODIMENTS

Figure 1:
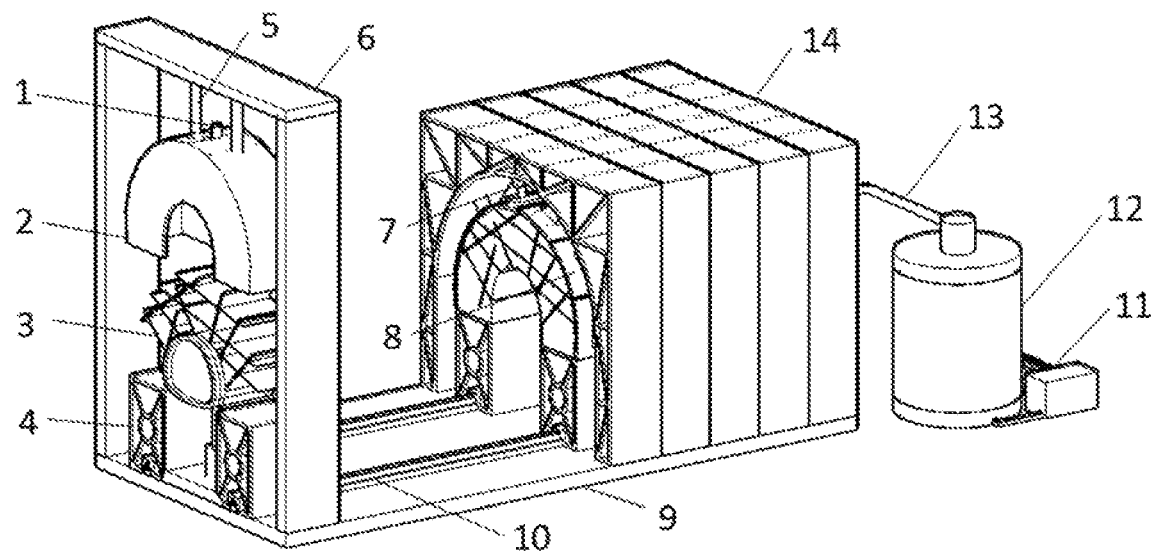
FIGS. 1 and 2 are schematic diagrams of an overall structure of the present invention.
Figure 2:
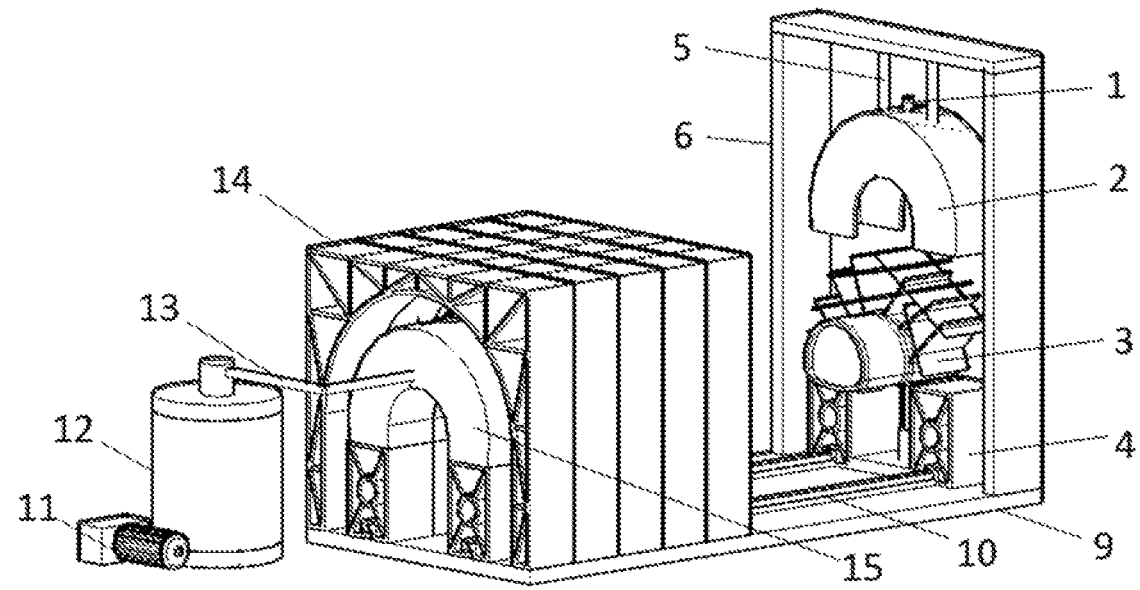
Figure 3:
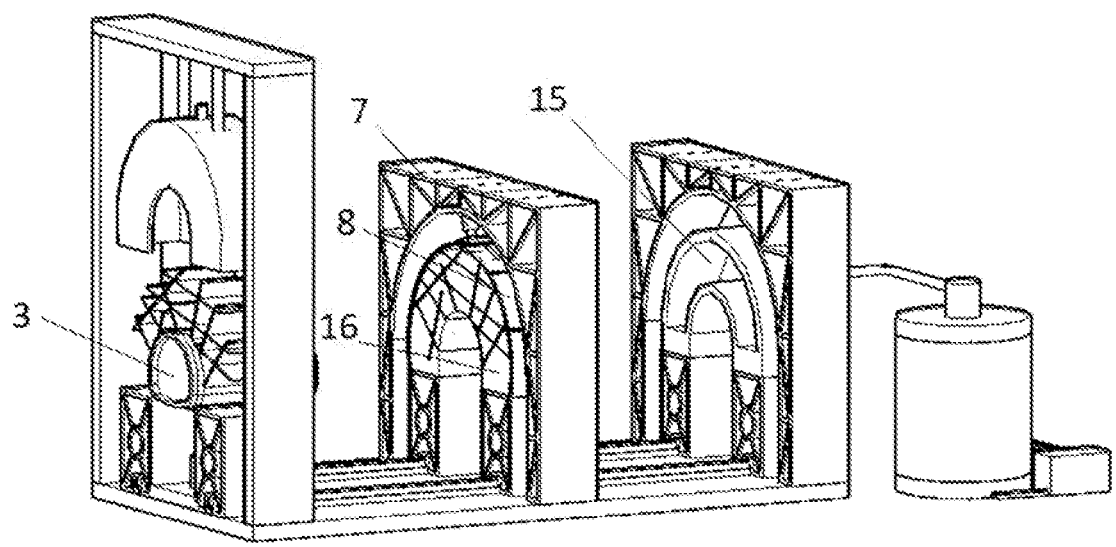
FIGS. 3 and 4 are schematic diagrams of a partial structure of the present invention.
Figure 4:
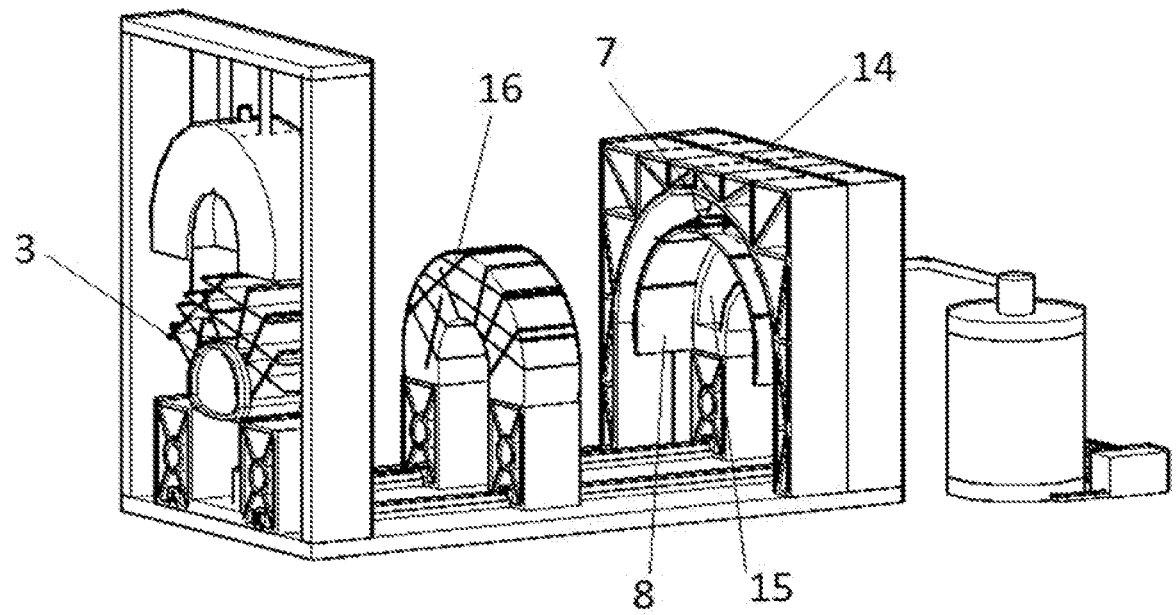
Figure 5:
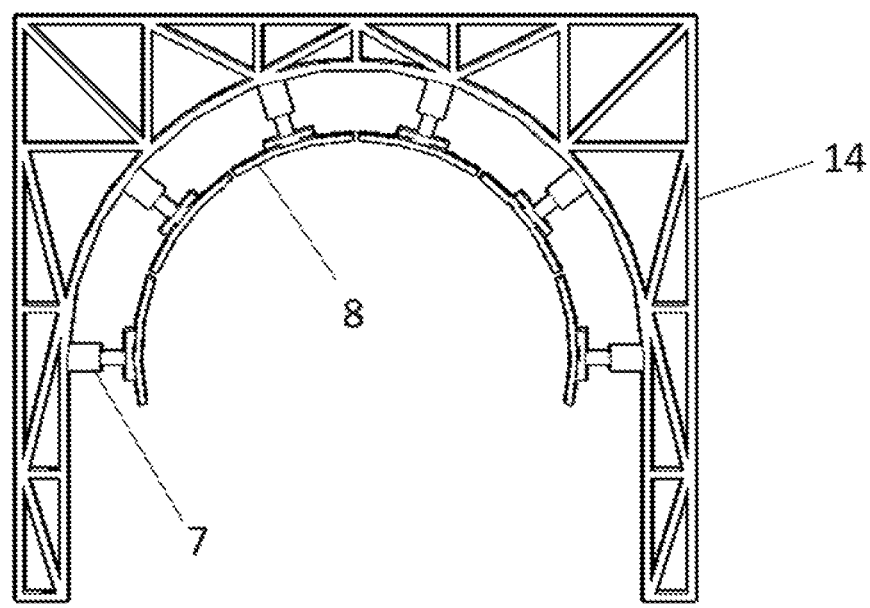
FIG. 5 is a schematic diagram of a confining pressure loading system of the present invention.
Figure 6:
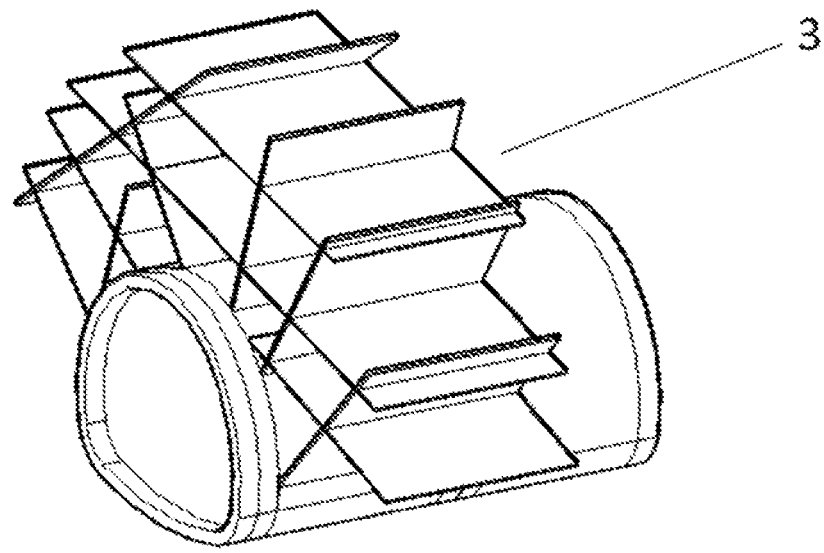
FIG. 6 is a schematic diagram of a cutterhead of the present invention.
Figure 7:
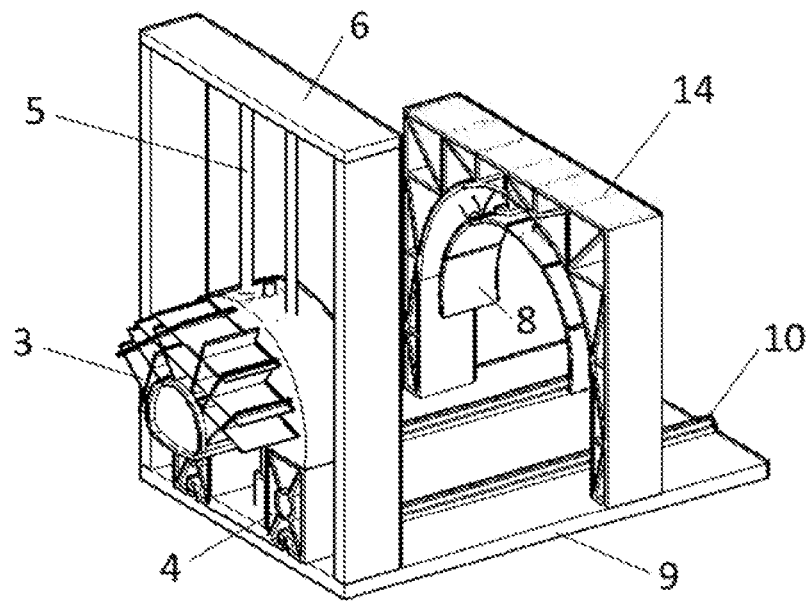
FIG. 7 is a schematic diagram of a material solidification process of the present invention.
Figure 8:
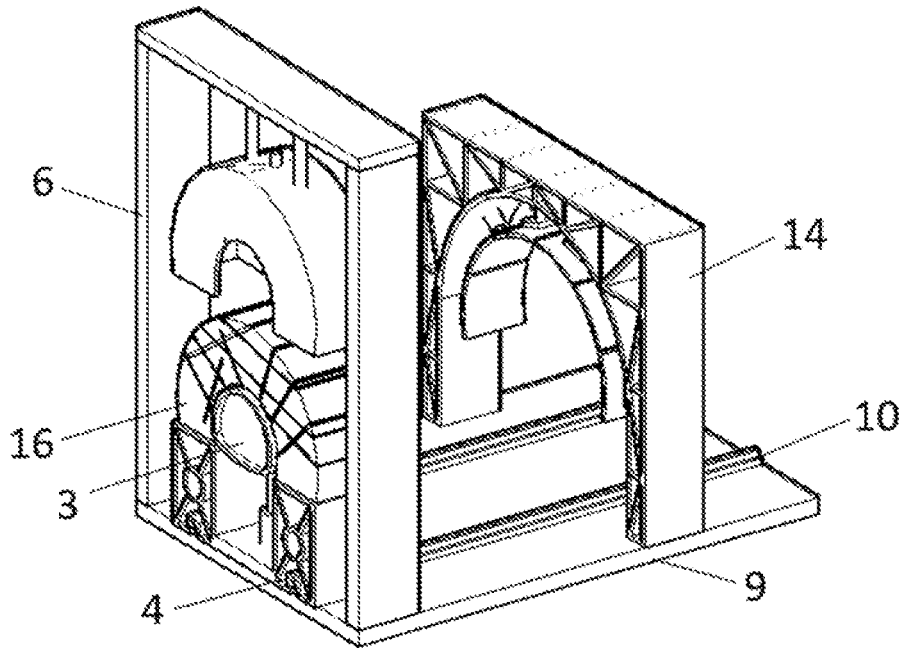
FIG. 8 is a schematic diagram of a rock fracture cutting process of the present invention.

The present invention will be further described below in conjunction with the drawings and embodiments:

As shown in FIGS. 1 and 2, a novel device for researching fractured rock mass collapse and rockfall and fracture water inrush in tunnels mainly includes (1) a fractured rock mass simulation system: a telescopic rod 5 is installed on an upper steel frame 6 and is connected with an upper die 2, the expansion and retraction of the telescopic rod 5 control the ascending and descending of the upper die 2, when the telescopic rod 5 expands, the upper die 2 descends and cooperates with a lower die to constitute a molding cavity of a simulative rock mass. A material injection port 1 is reserved above the upper die 2. A bottom support 4, the lower die and the upper die 2 constitute a closed chamber.

The upper die 2 is arched, and the upper surface of the lower die is also curved, and the formed closed chamber is arched, as there is substantially no dead angle in the closed chamber. Thus, when the material is injected from the material injection port 1, a solidified compact simulative rock mass material can be obtained in the molding cavity.

A cutterhead 3 is movably installed on the lower die through a guide rail, and the guide rail is horizontally arranged. When a liquid similar material is injected, such as hot melt paraffin, into the molding cavity, the simulative rock mass is obtained after the material solidifies, and the cutterhead 3 is slid toward the obtained simulative rock mass along the guide rail to cut the simulative rock mass so as to generate fractures in the rock mass. Since the fracture in the rock mass generally starts from a point and radially extends outward to form a plurality of cracks, in order to better simulate the internal cracks of the rock mass, the cutterhead 3 herein should not be a single blade, and should be a reticular blade assembly formed by assembling a plurality of staggered blades. The blade angles can be adjusted according to the block cutting requirements to generate different groups of structural surfaces.

(2) Surrounding rock pressurization system: an external steel rack 14 acts as a counter-force device, a hydraulic jack 7 is installed in the external steel rack to act on the surface of the formed fractured rock mass 16. The magnitude of the acting force of the hydraulic jack 7 is adjusted through a numerical control system to realize demands of rock mass stress in different environments. The top inner surface of the external steel rack 14 is arched, and a plurality of hydraulic jacks are installed along the top outer surface of the steel rack 14. The model numbers of the hydraulic jacks 7 are preferably the same, so that the lower ends of the hydraulic jacks 7 are all connected with curved plates. The plurality of curved plates are connected end to end to form an arch structure, the end-to-end connection here is not strictly required, and a certain gap may be reserved between adjacent curved plates. When these hydraulic jacks 7 pressurize the obtained simulative rock mass through the curved plates, the pressure distribution can be uniform, and the force in the tunnel can be more accurately simulated.

(3) Water source loading system: a water storage tank 12 behind the external steel rack 14 communicates with the a water storage structure 15 simulated in the steel rack 14 through a water guide tube 13 to realize the research on the water guide structure of the rock fracture. A pressurization water pump 11 is installed in the water storage tank 12. The water pressure is controlled by adjusting a pressure valve so as to research the influence of the water pressure on the water inrush criteria. The water is transported to the water storage structure 15 by the pressurization water pump, and the water pressure in the water storage structure 15 is adjusted by adjusting a pressure control valve. The relationship between the simulated fractured rock mass and the water pressure in the water storage structure 15 is observed to research the influence of the water pressure on the water inrush criteria.

(4) Two slide rails are installed on a bottom plate 9, and the two slide rails are installed side by side. The bottom support 4 is installed on the two slide rails to achieve the free sliding of the bottom support 4 on the rack bottom plate 9, and the fabrication and slicing of the multi-truss simulative rock mass are achieved.

The steel frame 6 and the rack bottom plate 9 are formed by splicing profile steel plates with bolt slots, and the lower portion of the steel frame 6 is fixed to the rack bottom plate 9 by bolts.

The steel rack 14 is formed by connecting and combining high-strength manganese steel members through high-strength bolts. The rack bottom plate 9 is formed by splicing, side by side, profile steel plates with bolt slots, and the steel frame is fixed to the required bolt slot position of the bottom plate 9 by high-strength bolts for the bottom plate.

The hydraulic jack 7 installed in the steel rack 14 acts on the surface of the formed rock mass through the curved plate 8, and a designed pressure value is input by a numerical control hydraulic loading system to control the magnitude of the force acting on the surface of the rock mass by the hydraulic jack 7 so as to meet the demands of crustal stress in different surrounding rock environments.

The simulative water storage structure in the steel rack 14 is composed of a steel frame at the outside. The internal space is arched and is consistent with the shape of the simulative rock mass. Then the water storage structure can be closely fitted with the rock mass.

Two or three horizontal slide rails are paved on the rack bottom plate 9. Actually, two horizontal slide rails can achieve the test purpose, and one more horizontal slide rail can better ensure the uniformity of sliding and avoid deflection in the process of sliding. After each simulative rock mass is formed, the simulative rock mass together with each support, slides along the sliding rail to the corresponding steel rack to bear the pressure applied by the hydraulic jack 7.

A test device of fractured rock mass collapse and rockfall and fracture water inrush includes the following steps:

(1) Profile steel plates with bolt slots are spliced side by side and assembled into the rack bottom plate 9 side by side, and paving two horizontal slide rails 10 on the bottom plate 9.

(2) The profile steel plates are spliced into a steel frame 6, and the lower part of the frame is fixed to the rack bottom plate 9 through bolts. The telescopic rod 5 is installed on the lower part of the steel frame and is fixed by bolts.

(3) The profile steel plates are welded into an arched upper die 2, and a circular material injection hole 1 is reserved above the upper die 2.

(4) Box type high-strength manganese steel members are connected and combined into the bottom support 4 through high-strength bolts, a groove is reserved in the lower part of the support 4, and the support 4 can move along the slide rails 10. A bracket is installed at the middle of the support 4, a cylindrical lower die is designed above the bracket, and the cutterhead 3 with the adjustable angle is installed on the front half of the lower die.

(5) High-strength manganese steel members are connected and assembled into the steel rack 14 by high-strength bolts, the hydraulic jack 7 is installed on the lower surface of the steel rack 14, and the curved plate 8 is installed at the other end of the hydraulic jack 7.

(6) The water storage tank 12 is installed behind the steel rack 14, and the water storage tank 12 is provided with the pressurization water pump 11 and communicates with the rock mass water storage structure 15 through the water guide tube 13.

(7) In the steel rack 14, a steel framework is assembled into the simulative rock mass water storage structure 15, the internal space is arched and is closely fitted with the simulative fractured rock mass 16.

Although the specific embodiments of the present invention has been described above with reference to the drawings, the protection scope of the present invention is not limited thereto, and those skilled in the art to which the present invention belongs should understand that various modifications or variations, which can made by those skilled in the art on the basis of the technical solutions of the present invention without any creative effect, still fall within the protection scope of the present invention.

The invention claimed is:

1. A fractured rock mass preparation device for a fractured rock mass test, the device comprising:
   a template comprising an upper die, and a lower die,
   a bottom support movably installed on a slide rail to which is fixed a water source loading device and to which is connected a surrounding rock pressurization device, and
   a cutterhead installed on a side face of the bottom support, wherein:
   the template is arranged above the bottom support, with the lower die of the template being fixed on the bottom support;
   the upper die is located above the lower die;
   the upper die, the lower die, and the bottom support constitute a molding cavity of a simulative rock mass;
   the cutterhead is movably installed on the lower die through a guide rail which is horizontally arranged;
   after a rock mass is formed, the cutterhead is configured to slide toward the rock mass to cut the rock mass to obtain a fractured rock mass;
   the fractured rock mass preparation device is fixed at one end of the slide rail, the other end of the slide rail is fixed to the water source loading device, and the water source loading device comprises:
   a water source;
   a rock mass water storage structure having an opening, a size of the opening being adapted to a size of the fractured rock mass formed by the cutterhead; and
   a water pump connected between the water source and the rock mass water storage structure; and
   the surrounding rock pressurization device comprises at least one bracket movably installed on the slide rail and a pressurization structure arranged below the bracket, a space for accommodating the fractured rock mass being reserved below the pressurization structure.

2. A test device of fractured rock mass collapse and fall-rock and fracture water inrush, comprising a fractured rock mass preparation device, a water source loading device, a surrounding rock pressurization device and a slide rail, wherein the fractured rock mass preparation device is fixed at one end of the slide rail, and the water source loading device is fixed on the other side of the slide rail;
   the fractured rock mass preparation device comprises a template, a cutterhead and a bottom support, the template being arranged above the bottom support, and the cutterhead being installed on a side face of the bottom support for cutting the formed rock mass to form the fractured rock mass;
   the water source loading device comprises a water source and a rock mass water storage structure, a water pump being connected between the water source and the rock mass water storage structure, an opening being formed in the rock mass water storage structure, and the size of the opening being adapted to the size of the fractured rock mass;
   the surrounding rock pressurization device comprises at least one bracket and a pressurization structure arranged below the bracket, a space for accommodating the fractured rock mass being reserved below the pressurization structure; and
   the bottom support and the bracket are both movably installed on the slide rail.

3. The test device according to claim 2, wherein when the formed fractured rock mass slides to the arched opening of the rock mass water storage structure to form seal fit, a test device for simulating fracture water inrush is formed, and the water pressure in the rock mass water storage structure is controlled through the water pump to simulate the fracture water inrush under different water pressures.

4. The test device according to claim 2, wherein template comprises an upper die and a lower die, the lower die is installed on a bottom bracket, and the upper die, the lower die and the bottom bracket form a molding cavity of the arched rock mass.

5. The test device according to claim 4, wherein the upper surface of the lower die is a semi-cylindrical molding surface, and the chamber of the upper die is arched.

6. The test device according to claim 4, wherein the cutterhead is movably installed on the lower die by the guide rail and is movable in the horizontal direction along the lower die; and the length of the lower die is greater than that of the cutterhead.

7. The test device according to claim 2, wherein the lower die is placed on two groups of bottom brackets, which are a first group of bottom brackets and a second group of bottom brackets, the first group of bottom brackets being fixed at an end of the slide rail, the second group of bottom brackets being movably installed on the slide rail, and the upper die, the lower side and the second group of bottom brackets constituting the molding cavity of the arched rock mass.

8. The test device according to claim 2, wherein the cutterhead is provided with a plurality of blades, and the blades are arranged in a stagger manner to generate joint fissures.

9. The test device according to claim 8, wherein the angles of the blades on the cutterhead are adjustable to generate different joint fissures.

10. The test device according to claim 2, wherein the bracket is a steel frame, and the lower surface of the steel frame is arched.

11. The test device according to claim 10, wherein the pressurization structure comprises multiple groups of pressurization devices, each group of pressurization devices comprising a hydraulic jack and a curved plate, one end of the hydraulic jack being fixed on the lower surface of the steel frame, and the other end of the hydraulic jack being fixedly connected with the curved plate.

12. The test device according to claim 11, wherein the multiple groups of pressurization devices are arranged in a row, and the plurality of curved plates are connected into an arch shape.

13. A test method of fractured rock mass collapse and rockfall and fracture water inrush, the method comprising the following steps:
   1) injecting similar materials into upper and lower dies to prepare a simulative rock mass, and separating the upper die from the simulative rock mass;
   2) sliding a cutterhead toward the simulative rock mass to cut the rock mass to obtain the fractured rock mass;
   3) separating the fractured rock mass from the lower die;
   4) moving the fractured rock mass to a rock mass water storage structure, and sealing the fractured rock mass with an opening of the rock mass water storage structure;
   5) injecting water into the rock mass water storage structure, and adjusting the internal water pressure to perform a fracture water inrush test;

6) pressurizing the fractured rock mass by using a surrounding rock pressurization device to perform a fracture collapse test;
or pressurizing the fractured rock mass during the fracture water inrush test; and
the order of the above steps can be adjusted as long as the test is not affected.

* * * * *